US008945215B2

(12) United States Patent
Basinger

(10) Patent No.: US 8,945,215 B2
(45) Date of Patent: Feb. 3, 2015

(54) ACCOMMODATING INTRAOCULAR LENS WITH A COMPRESSIBLE INNER STRUCTURE

(75) Inventor: Brooke C. Basinger, Long Beach, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 4 days.

(21) Appl. No.: 13/468,599

(22) Filed: May 10, 2012

(65) Prior Publication Data

US 2013/0304202 A1 Nov. 14, 2013

(51) Int. Cl.
*A61F 2/16* (2006.01)

(52) U.S. Cl.
USPC .......... 623/6.37; 623/6.4; 623/6.43; 623/6.49

(58) Field of Classification Search
USPC .............. 623/6.37, 6.39, 6.4, 6.42–6.43, 6.46
See application file for complete search history.

(56) References Cited

U.S. PATENT DOCUMENTS

| 4,361,913 A | 12/1982 | Streck |
| 4,370,760 A | 2/1983 | Kelman |
| 4,373,218 A | 2/1983 | Schachar |
| 4,442,553 A | 4/1984 | Hessburg |
| 4,512,040 A | 4/1985 | McClure |
| 4,560,383 A | 12/1985 | Leiske |
| 4,562,600 A | 1/1986 | Ginsberg et al. |
| 4,615,701 A | 10/1986 | Woods |
| 4,641,934 A | 2/1987 | Freeman |
| 4,731,078 A | 3/1988 | Stoy et al. |
| 4,769,035 A | 9/1988 | Kelman |
| 4,813,955 A | 3/1989 | Achatz et al. |
| 4,842,601 A | 6/1989 | Smith |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,963,148 A | 10/1990 | Sulc et al. |
| 4,994,082 A | 2/1991 | Richards et al. |
| 4,994,083 A | 2/1991 | Sulc et al. |
| 5,047,051 A | 9/1991 | Cumming |
| 5,152,789 A | 10/1992 | Willis |
| 5,275,623 A | 1/1994 | Sarfarazi |
| 5,476,514 A | 12/1995 | Cumming |

(Continued)

FOREIGN PATENT DOCUMENTS

| CH | 681687 A5 | 5/1993 |
| EP | 766540 A1 | 4/1997 |

(Continued)

OTHER PUBLICATIONS

English translation of WO93/05733A1.

(Continued)

*Primary Examiner* — David H Willse
*Assistant Examiner* — Tiffany Shipmon
(74) *Attorney, Agent, or Firm* — Abbott Medical Optics Inc.

(57) ABSTRACT

An accommodating intraocular lens for providing a range of accommodative vision contains an optic and a haptic. The haptic includes a plurality of arms coupled to a compressible inner structure. The compressible inner structure of the haptic is configured to exert a compressive force on the optic in response to an ocular force to provide accommodation. The compressible inner structure can include a plurality of arcuate segments that join to form a ring in the fully compressed state or a sinusoidal ring having a varying radial dimension.

19 Claims, 13 Drawing Sheets

(56) References Cited

U.S. PATENT DOCUMENTS

| | | |
|---|---|---|
| 5,489,302 A | 2/1996 | Skottun |
| 5,496,366 A | 3/1996 | Cumming |
| 5,607,472 A | 3/1997 | Thompson |
| 5,628,795 A | 5/1997 | Langerman |
| 5,674,282 A | 10/1997 | Cumming |
| 5,984,962 A | 11/1999 | Anello et al. |
| 6,013,101 A | 1/2000 | Israel |
| 6,051,024 A | 4/2000 | Cumming |
| 6,083,261 A | 7/2000 | Callahan et al. |
| 6,110,202 A | 8/2000 | Barraquer et al. |
| 6,117,171 A | 9/2000 | Skottun |
| 6,120,538 A | 9/2000 | Rizzo, III et al. |
| 6,197,059 B1 | 3/2001 | Cumming |
| 6,200,342 B1 | 3/2001 | Tassignon |
| 6,217,612 B1 | 4/2001 | Woods |
| 6,299,641 B1 | 10/2001 | Woods |
| 6,443,985 B1 | 9/2002 | Woods |
| 6,930,838 B2 | 8/2005 | Schachar |
| 7,097,660 B2 | 8/2006 | Portney |
| 7,150,759 B2 | 12/2006 | Paul et al. |
| 7,179,292 B2 | 2/2007 | Worst et al. |
| 7,220,279 B2 | 5/2007 | Nun |
| 7,503,938 B2 | 3/2009 | Phillips |
| 7,815,678 B2 | 10/2010 | Ben Nun |
| 2003/0004569 A1 | 1/2003 | Haefliger |
| 2004/0082993 A1 | 4/2004 | Woods |
| 2004/0082995 A1 | 4/2004 | Woods |
| 2004/0111153 A1 | 6/2004 | Woods et al. |
| 2005/0018504 A1 | 1/2005 | Marinelli et al. |
| 2005/0021139 A1 | 1/2005 | Shadduck |
| 2005/0131535 A1 | 6/2005 | Woods |
| 2006/0238702 A1 | 10/2006 | Glick et al. |
| 2007/0078515 A1 | 4/2007 | Brady |
| 2007/0100444 A1 | 5/2007 | Brady et al. |
| 2007/0106381 A1 | 5/2007 | Blake |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2008/0161913 A1 | 7/2008 | Brady et al. |
| 2008/0161914 A1 | 7/2008 | Brady et al. |
| 2009/0012609 A1 | 1/2009 | Geraghty et al. |
| 2010/0094415 A1* | 4/2010 | Bumbalough ............... 623/6.51 |
| 2011/0029074 A1 | 2/2011 | Reisin et al. |
| 2011/0040379 A1 | 2/2011 | Bumbalough |
| 2011/0257742 A1* | 10/2011 | Bumbalough et al. ....... 623/6.43 |

FOREIGN PATENT DOCUMENTS

| | | |
|---|---|---|
| EP | 766540 B1 | 8/1999 |
| JP | 2126847 A | 5/1990 |
| WO | WO0119288 A1 | 3/2001 |
| WO | WO0219949 A2 | 3/2002 |
| WO | WO2005115278 A1 | 12/2005 |
| WO | 2008108524 A1 | 9/2008 |
| WO | 2011017322 A1 | 2/2011 |

OTHER PUBLICATIONS

U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.
International Search Report and Written Opinion for Application No. PCT/US2013/040504, mailed on Jul. 30, 2013, 11 pages.

* cited by examiner

ACCOMMODATING INTRAOCULAR LENS WITH A COMPRESSIBLE INNER STRUCTURE

BACKGROUND OF THE INVENTION

1. Field of the Invention

The present invention relates generally to intraocular lenses, and more specifically to intraocular lenses for providing accommodative vision to a human or animal subject.

2. Description of the Related Art

A young human eye is generally capable of focusing over a wide rage of distances in a process known as accommodation. Optically, the range of positions is largely accomplished by changing the power of the natural lens. The natural lens is deformed by the eye to modify the power. A human eye can suffer diseases that impair a patient's vision. For instance, a cataract may increase the opacity of the lens, which impairs vision and may ultimately result in blindness. To restore the patient's vision, the opaque lens may be surgically removed and replaced with an artificial intraocular lens, or IOL. An IOL may also be implanted to treat presbyopia or for other elective ocular surgical procedures.

Monofocal IOLs have a single focal length, or equivalently, a single power. Single focal length IOLs cannot accommodate. Rather, they provide clear vision only over a limited range of distances. As a result, distant objects may appear in focus, while objects at a normal reading distance from the eye may appear blurred.

Vision over a broader range of distances can be obtained with multifocal lenses. Multifocal lenses provide different foci enabling the patient to see objects at multiple distances. Aspheric lenses can be configured to provide an extended depth of focus. Such lenses can improve vision, but there may also be an associated reduction in visual acuity or overall visual quality.

Another approach is to use an accommodating IOL, which can adjust its axial position and/or optical power within a range in response to action of ciliary muscles in the eye. As a result, the patient can focus on objects in a range of distances from the eye, rather than at one or more discrete distances. This ability to accommodate is of tremendous benefit for the patient, and more closely approximates the patient's natural vision. One of the challenges in accommodating IOL's is providing a sufficient range of accommodation with the limited amount of ciliary muscle force. In various implementations of the accommodating IOL's, these small forces are transferred through a haptic or support structure that absorbs a certain amount of the force. Haptic or support structures that maximize the shape changing and/or axial position shifting capability of the accommodating IOL are desired.

SUMMARY OF THE INVENTION

The systems, methods and devices of the disclosure each have several innovative aspects, no single one of which is solely responsible for the desirable attributes disclosed herein.

Embodiments disclosed herein are directed to devices and methods for providing accommodative vision. In one aspect, an intraocular lens is provided that comprises an adjustable optic adapted to focus light on the retina when disposed in the eye and a haptic or mounting structure that is operably coupled to the optic. In various implementations of the IOL, the adjustable optic can comprise an elastic material that can be deformed by ocular forces. The haptic or mounting structure can comprise a material that is stiffer than the material of the adjustable optic. The stiffer haptic or mounting structure can include an inner structure that can exert a compressive force on the deformable optic to change the shape of the deformable optic to provide accommodation. In various implementations, the inner structure can be discontinuous and/or include a plurality of arcuate segments to enhance accommodation as discussed below.

In one embodiment, an intraocular lens comprises an optic adapted to focus light on the retina when disposed in the eye, the optic having an adjustable zone intersected by a central optical axis of the optic, and a haptic comprising: an inner annular member disposed adjacent to or inside the adjustable zone of the optic, the inner annular member comprising a continuous inner perimeter in a fully compressed state and a plurality of spaced apart arcuate segments in a relaxed state; and a plurality of arms extending away from the inner annular member, wherein the intraocular lens is adapted to respond to ocular forces to adjust the power of the optic from a distance vision power in the relaxed state to a near vision power in a fully accommodated state. Each of the arms may comprise a proximal end extending away from an outer side of the inner annular member. The distal end of each of the arms may be coupled with a continuous ring such that the inner annular member is disposed between the ring and the optic. The continuous ring may comprise of a plurality of straight segments extending transverse to a longitudinal axis of each arm, the straight segments being joined at a location between adjacent arms. The continuous ring may comprise a wavy member comprising at least one inflection disposed between adjacent arms. The continuous ring may comprise a sinusoidal configuration. Each arm of the plurality of arms may extend along a direction perpendicular to the optical axis. There may be between four and twelve arms spaced apart by a constant amount extending symmetrically away from the adjustable zone. The adjustable zone may be adapted to provide at least 2 Diopters of add power, preferably 4 Diopters.

In another embodiment, an intraocular lens comprises an optic disposed about a central optical axis and adapted to focus light on the retina when disposed in the eye, the optic having an adjustable zone and a haptic comprising: a plurality of arms, each arm having an inner end adjacent to the adjustable zone and an elongate body extending away from the inner end; and an inner member comprising a continuous inner surface surrounding the adjustable zone, the inner surface being located a varying distance from the central optical axis, wherein the intraocular lens is adapted to respond to ocular forces to adjust the power of the optic from a distance vision power zone toward a near vision power. The inner member may comprise a sinusoidal configuration, wherein each of the arms is coupled with a peak of the sinusoidal inner member. Or, each of the arms may be coupled with a valley of the sinusoidal inner member. Each of the arms extends away from an outer portion of the inner member corresponding to a portion of the inner surface that is spaced farther away from the central optical axis than are adjacent portions of the inner surface. Or, each of the arms may extend away from an outer portion of the inner member corresponding to a portion of the inner surface that is closer to the central optical axis than are adjacent portions of the inner surface.

In another embodiment, an intraocular lens comprises: a deformable optic having a relaxed configuration including a first radius of curvature characteristic and a compressed configuration including a second radius of curvature characteristic, the deformable optic adapted to be deformed from the relaxed configuration to the compressed configuration by ocular forces; and a plurality of haptic arms that can engage and apply a radial compressive force to axially deform the deformable optic, each of the plurality of haptic arms including a proximal arcuate section that can engage an outer or an inner periphery of the deformable optic and a distal portion that can engage an evacuated capsular bag, the proximal arcuate section of each of the plurality of haptic arms including an arcuate region that extends along the radial direction. The proximal arcuate section of each of the plurality of haptic arms may include an arcuate region that extends along the circumferential direction, and the proximal arcuate sections of each of the plurality of haptic arms can join to form a continuous structure when the deformable optic is in the compressed configuration. An outer ring may connect the distal portions of each of the plurality of haptic arms. The outer ring may include a plurality of straight segments extending transverse to a longitudinal axis of each arm, the straight segments being joined at a location between adjacent arms. Or, the outer ring may comprise a wavy member comprising at least one inflection disposed between adjacent haptic arms. The outer ring may comprise a sinusoidal configuration.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Embodiments disclosed herein may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE PREFERRED EMBODIMENT

In a healthy human eye, the natural lens is housed in a structure known as the capsular bag. During natural accommodation, the capsular bag is acted on by a ciliary muscle and zonular fibers (also known as zonules) in the eye, which can pull on the capsular bag to change its shape. The motion of the capsular bag generally deforms the natural lens in order to change its power and/or the location of the lens, so that the eye can focus on objects at varying distances away from the eye in a process known as accommodation.

I. Intraocular Lenses Adapted to Accommodate by Changing the Shape of an Optic

Embodiments described herein are directed to intraocular lenses that advantageously use ocular forces, such as those produced by the ciliary muscle, zonules, and/or capsular bag, to change the shape of the lens optic. Such an accommodating lens may produce vastly improved vision over a lens with a fixed power and location that does not accommodate. However, the term "ocular force" does not necessarily refer only to forces produced by ciliary muscle, zonules, and/or capsular bag. As used herein the term "ocular force" is a broad term that includes a force that is sufficient to provide accommodation in the eye of a healthy human subject.

Figure 1:
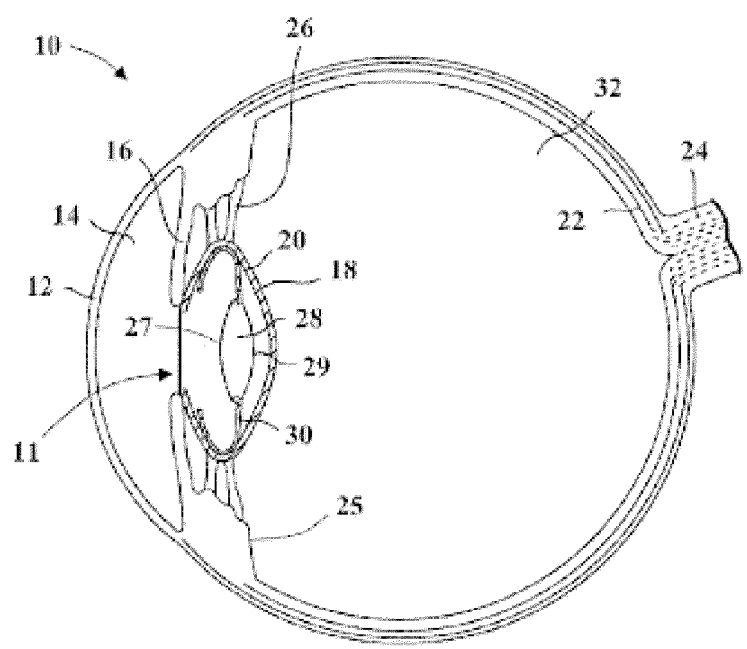
FIG. 1 is a cross-sectional view of a human eye having an implanted intraocular lens in an accommodative or "near" state.

FIG. 1 shows a human eye 10, after an accommodating intraocular lens 11 is implanted. Prior to surgery, the natural lens occupies essentially the entire interior of the capsular bag 18. After surgery, the capsular bag 18 may house the intraocular lens 11. Alternatively, the intraocular lens 11 may be configured to directly engage the zonules or ciliary muscle.

Light enters from the eye 10 from the left in FIG. 1 and passes through the cornea 12, the anterior chamber 14, the pupil (defined by the inner edge of the iris 16), and impinges on the intraocular lens 11. After passing through the intraocular lens 11, light exits the posterior wall 20 of the capsular bag 18, passes through the vitreous body 32, and strikes the retina 22, which detects the light and converts it to a signal transmitted through the optic nerve 24 to the brain.

A well-corrected eye forms an image at the retina 22. If the intraocular lens 11 has too much or too little power, the image shifts axially along the optical axis away from the retina, toward or away from the lens 11. Note that the total power of the eye (e.g., including the combined power of cornea 12 and the intraocular lens 11) required to focus on a close or near object is more than the power required to focus on a distant or far object. The difference between the "near power" and "far power" is known typically as the range of accommodation or the add power. A typical range of accommodation or add power is about 2 to 4 diopters, but may be significantly larger for children.

The intraocular lens 11 may be designed so that its relaxed or natural state is the "far" or "distant" condition (sometimes referred to as a "disaccommodative biased" intraocular lens), the "near" condition (an "accommodative biased" intraocular lens), or some condition in between the two. As used herein, the terms "natural state", "natural configuration", "relaxed state", and "relaxed condition" can refer to a condition of an intraocular lens in which no external forces (e.g., ocular forces from the ciliary muscle, zonules, or capsular bag) are acting upon the intraocular lens 11 or the optic 48 of an intraocular lens 40 (discussed below).

The capsular bag 18 is acted upon by the ciliary muscle 25 via the zonules 26, which distort the capsular bag 18 by stretching it radially in a relatively thick band about its equator. Experimentally, it is found that the ciliary muscle 25, zonules 26, and/or capsular bag 18 typically exert a total radial force of up to about 10 grams of force, which is generally distributed uniformly around an equatorial region of the capsular bag 18. In some patients, non-uniform forces may be applied to the capsular bag 18, for example, due to damage of the zonules, which can cause astigmatism or other optical aberrations.

Although the range of ocular force may vary from patient to patient, the range of accommodation for each subject is generally limited by the total ocular force available. Therefore, it is generally preferred that the intraocular lens 11 be configured to vary its power over the full range of accommodation in response to this limited range of ocular forces (e.g., to provide at least 3 Diopters or 4 Diopters of accommodative power). In other words, it is desirable to have a relatively large change in power for a relatively small driving force. Alternatively, the effective range of accommodation may be increased by incorporating a lens having a multifocal or extended depth-of-focus configuration.

The intraocular lens 11 generally has an optic 28 made of a transparent, deformable and/or elastic material and a haptic 30 configured to hold the optic 28 in place and to mechanically transfer forces from the eye (e.g., from the capsular bag 18 or ciliary muscle 25) to the optic 28. The interface between the haptic 30 and the optic 28 can vary, for example being configured to maximize deformation of the optic 28 for a given ocular force.

When the eye 10 is focused on a relatively close object, as shown in FIG. 1, the ciliary muscle 25 is compressed, which causes the zonules 26 to relax and allow the equatorial region of the capsular bag 18 to contract. The capsular bag 18 in this state is thicker at its center and has more steeply curved sides. As a result, the power of the lens 11 can be relatively high (e.g., the radii of curvature of one or both of the lens surfaces can decrease, and/or the lens can become thicker, and/or the lens can move axially), placing the image of the relatively close object at the retina 22. Note that if the lens could not accommodate, the image of the relatively close object would, for an emmetropic eye, be located behind the retina, and would appear blurred. Also, if the eye has aberrations such as astigmatism, uniform power in all diameters or segments of the lens would not produce satisfactory vision. For some diameters or segments, light would focus at the retina and for others light would focus behind or in front of the retina.

Figure 2:
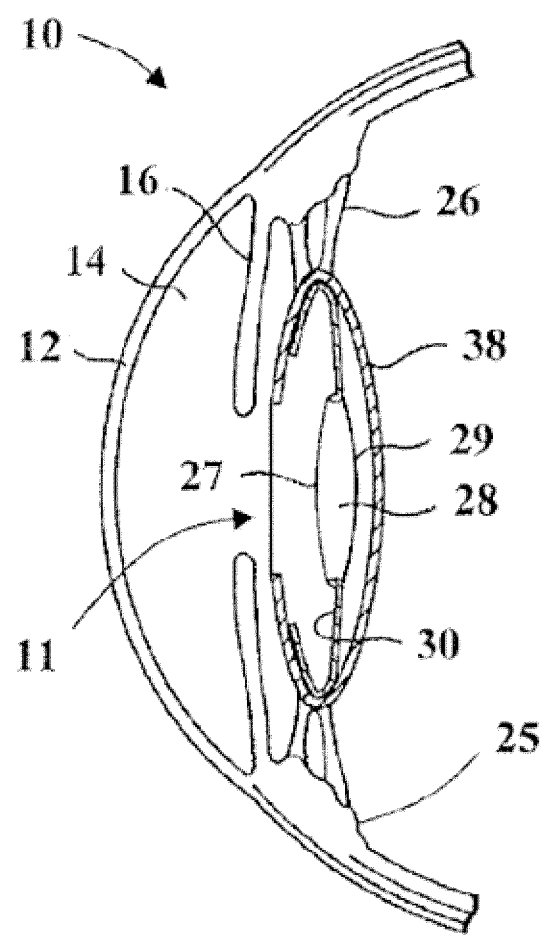
FIG. 2 is a cross-sectional view of the human eye of FIG. 1 in a disaccommodative or "far" state.

FIG. 2 shows a portion of the eye 10 focused on a relatively distant object. To focus on the distant object, the zonules 26 are retracted and the shape of the capsular bag 38 is thinner at its center and has less steeply curved sides. This can reduce the power of the lens 11 by flattening (e.g., increasing radii of curvature and/or thinning the lens, and/or moving the lens axially), placing the image of the relatively distant object at the retina (not shown).

For both the "near" case of FIG. 1 and the "far" case of FIG. 2, the accommodating intraocular lens deforms and changes shape in response to the ciliary muscle 25 and/or to the distortion of the capsular bag 18. For the "near" object, the haptic 30 compresses the optic 28, increasing the thickness of the optic 28 at its center and more steeply curving its anterior face 27 and/or its posterior face 29. As a result, the lens power increases. As discussed below in connection with FIG. 4A-6F, inner portions of the haptic 30 can be configured to minimize loss of force so that a high percentage of ocular force applied to the outer edge of the haptic 30 is transferred and applied to the optic. For the "far" object, the haptic 30 expands, pulling on the optic 28 at its edge or reducing a compressive force thereon, and thereby decreasing the thickness of the optic 28 at its center and less steeply curving (e.g., lengthening one or both radius of curvature) its anterior face 27 and/or its posterior face 29. As a result, the lens power decreases.

The specific degrees of change in curvature of the anterior and posterior faces 27, 29 depend on the nominal curvatures. Although the optic 28 is drawn as bi-convex, it may be plano-convex, meniscus or other lens shapes in other embodiments. In all of these cases, the optic 28 is compressed or expanded by forces from the haptic at or inside the edge and/or faces of the optic 28. In addition, there may be some axial movement of the optic 28. In various embodiments, the haptic 30 may be configured to transfer the generally symmetric radial forces symmetrically to the optic 28 to deform the optic 28 in a spherically symmetric way. In alternate embodiments, the haptic 30 may be configured to transfer the generally symmetric radial forces asymmetrically to the optic 28 to deform the optic 28 in a spherically asymmetric way.

The accommodating intraocular lens illustrated in FIGS. 1 and 2 are configured to occupy almost the entire volume of the capsular bag 18 after the natural lens is removed. In various embodiments of an accommodating intraocular lens that is configured to occupy the entire volume of the capsular bag 18, the size (for example, weight, area, or volume) of the haptic 30 may be greater than the size of the optic 28. In such embodiments, a fraction of the ocular force may be absorbed by the haptic and thus not used to deform the optic 28. Accordingly, it may be advantageous to have haptics that have a smaller footprint, are light-weight and can transfer most of the compressive ocular force to the optic without absorbing a significant amount of the compressive ocular force.

Figure 3A:
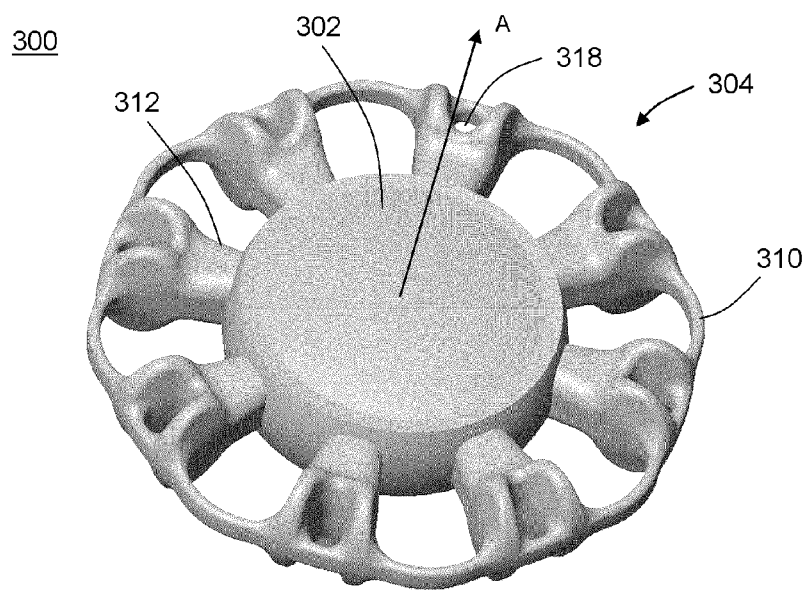
FIG. 3A is an isometric view of an accommodating intraocular lens showing an optic operably coupled to a haptic.

FIG. 3A illustrates an example of an accommodating intraocular lens 300 that can transfer ocular forces to the optic efficiently. The accommodating IOL 300 illustrated in FIGS. 3A and 3B comprises a haptic or a support structure 304 coupled to an optic 302 disposed about an optical axis A. Haptic 304 can change the shape and/or axial location of the optic 302, thereby providing a change in optic power and/or focal plane location of optic 302. The haptic or support structure 304 is substantially planar in the vicinity of the optic 302. In various implementations, the haptic or support structure 304 may not extend to the anterior or the posterior of the optic 302.

Figure 3B:
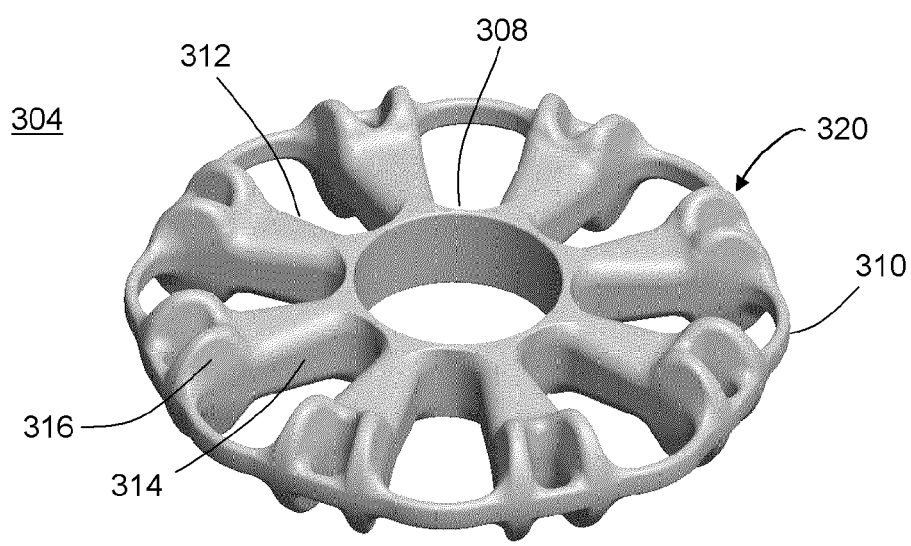
FIG. 3B is an isometric view of the haptic only from the intraocular lens shown in FIG. 3A, the haptic including an inner ring.

FIG. 3B is an isometric view of the haptic 304 only from the intraocular lens 300 shown in FIG. 3A. Haptic 304 includes an inner structure 308 and an outer structure 310 and a plurality of arms 312 connecting or coupling structures 308 and 310 to one another in a way that efficiently and effectively transfers ocular forces to the optic 302. Arms 312 each include a proximal end 314 coupled or connected to inner structure 308 and a distal end 316 coupled or connected to outer structure 310. In various embodiments, the arms 312, the inner structure 308 and/or the outer structure 310 can be compressible in response to the ocular force. In the embodiment illustrated in FIG. 3B, the inner structure 308 is a central ring that is coupled to the optic 302 and is configured to be compressible in response to ocular forces to deform or move the optic 302. As referred to herein the term "compressible" is a broad term that includes the ability of a structure to deform, bend or move to efficiently transfer a compressive force to an optic, and may or may not include a reduction in volume of the structure being compressed.

The arms 312 can have bifurcated distal ends 316. The bifurcated distal ends 316 of the arms 312 can be effective in reducing the mass of the outer structure 310. The distal end 316 of the arms 312 can bulge axially as compared to the proximal end 314. The outer structure 310 can have a peripheral region 320 that is arcuate in cross-section, for example, to engage a larger portion of the capsular bag. The relatively large axial thickness of peripheral region 320 (or, large axial extent measured as the distance of the portion of the arm along an axis that is normal to the optical axis) can be effective in transferring much of the forces produced by capsular bag 18 and/or zonules 26, since capsular bag 18 is engaged over a large axial extent. Thus, the outer structure 310 can engage a large extent or area of capsular bag 18, while also providing skeletal structure with a relatively low mass. The low mass of outer structure 310 results in a haptic that can effectively transfer the compressive ocular force to the optic without absorbing a significant portion of the ocular force. The outer structure 310 can be compressible and conform to changes in the shape of capsular bag 18 during accommodation. This, in turn, can allow more of the forces produced by the changing shape of capsular bag 18 to be coupled into haptic 304 and transferred into changing the shape and optical power of optic 302.

A possible advantage of having a haptic similar to haptic 304 is that significantly less ocular force is absorbed by the haptic itself such that more of the ocular force is used to deform and/or move the optic 302 to produce a range of powers in response to the ocular force. In various embodiments of the accommodating intraocular lens 300 illustrated in FIGS. 3A and 3B, to reduce the amount of ocular force that is absorbed by the haptic 304, the haptic 304 can be partly or wholly compressible such that the compressive ocular force is efficiently transferred to the optic 302. The haptic 304 can be similar to the haptic structures disclosed in U.S. application Ser. No. 12/849,451 titled "Intraocular Lens and Methods for Providing Accommodative Vision," which published as U.S. Publication No. 2011/0040379. The entire disclosure of the above-mentioned application is incorporated herein by reference.

As discussed in connection with FIGS. 4A-6F below, IOLs with haptic structures that can efficiently transfer the compressive ocular forces to the optic and advantageously provide the same accommodative effect as the accommodating intraocular lenses described with reference to FIGS. 1-3B with a smaller amount of ocular force.

II. Intraocular Lenses with Haptics Configured to Enhance Force Transfer

The embodiments of haptics for an intraocular lens illustrated in FIGS. 4A-6F are configured to engage and apply a radial compressive force to deform the optic radially and/or axially. For example, the haptics can be configured to squeeze the optic radially such that the optic bulges out axially. Various embodiments of the haptics can include structures that are sufficiently compressible such that most of the ocular force is transferred to the optic without being absorbed by the haptic. For example, as discussed in greater detail below, the haptics illustrated in FIGS. 4A-5B include an inner structure that is sinusoidal or wavy in the radial and/or axial direction which can efficiently transfer the compressive ocular force to the optic. As another example, as discussed in greater detail below, the haptics illustrated in FIGS. 6A-6F include a plurality of segments that protrude into the optic. Under the influence of a compressive ocular force, the plurality of segments can move or deform (for example, stretch or extend) to compress the optic. The plurality of segments can form a ring when the optic is fully compressed.

A. Haptics Including a Continuous Structure Adjacent to the Optic

Figure 4A:
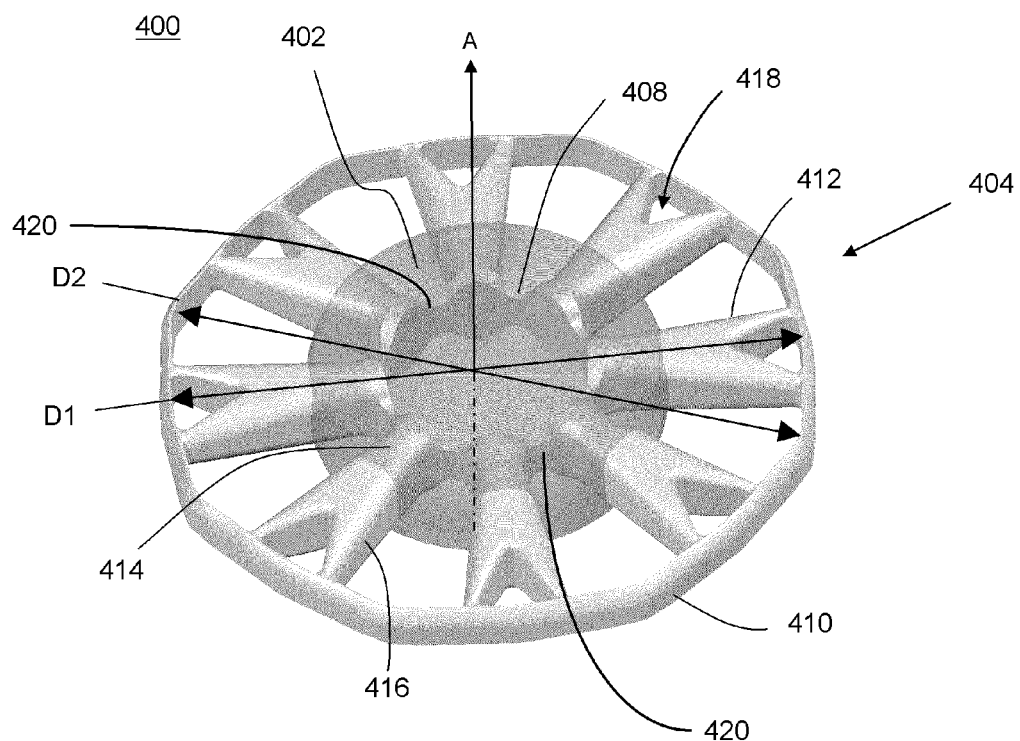
FIG. 4A is an isometric view of an accommodating intraocular lens showing an optic operably coupled to a haptic including an inner ring.
Figure 4B:
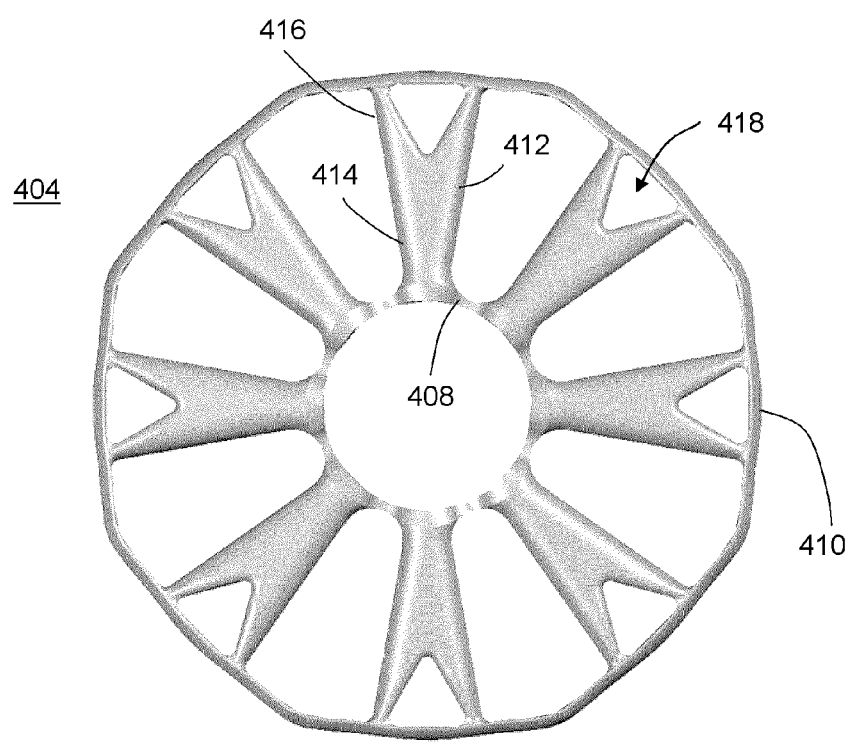
FIG. 4B is a plan view of the haptic only from the intraocular lens shown in FIG. 4A, the inner ring of the haptic is sinusoidal in the axial direction.
Figure 4C:
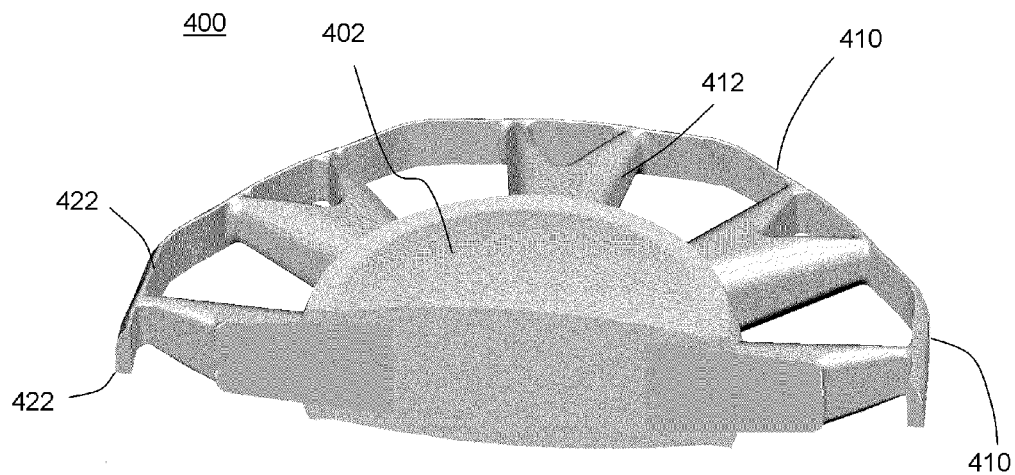
FIG. 4C is a cross-sectional isometric view through the section D1 of the intraocular lens illustrated in FIG. 4A showing a portion of the haptic protruding into the optic.

FIGS. 4A-4C, illustrate an embodiment of an accommodating IOL 400 comprising a haptic or a support structure 404 coupled to an optic 402 disposed about an optical axis A. The haptic 404 is configured to effectively transfer an ocular force from a human or animal eye to optic 402 to produce a range of powers in response to an ocular force. Haptic 404 includes an inner structure 408 and an outer structure 410 and a plurality of arms 412 connecting or coupling structures 408 and 410 to one another to efficiently and effectively transfer the ocular force to changing the shape and/or axial location of optic 402, thereby providing a change in optic power and/or focal plane location of optic 402. Arms 412 each include a proximal end 414 coupled or connected to inner structure 408 and distal end 416 coupled or connected to outer structure 410. Although the outer structure 410 and the arms 412 are shown to be planar, in various embodiments, the outer structure 410 and the arms 412 can have a structure similar to the outer structure 310 and the arms 312 discussed above in connection with FIG. 3B and the haptic structures disclosed in U.S. application Ser. No. 12/849,451 titled "Intraocular Lens and Methods for Providing Accommodative Vision," which published as U.S. Publication No. 2011/0040379. The entire disclosure of the above-mentioned application is incorporated herein by reference.

In contrast to the constant axial height/cylindrical inner structure 308 of the haptic 304 that is illustrated in FIG. 3B, the inner structure 408 of the embodiments illustrated in FIGS. 4A-4C is sinusoidal in the axial direction such that the inner structure 408 has a constant radial dimension but a varying axial thickness. As compared to the constant axial height/cylindrical inner structure 308, the sinusoidal inner structure 408 is weakened in the areas 420 where the axial thickness is reduced. The weakening of the inner structure 408 can result in an easily compressible structure which would allow the same accommodative effect as the accommodating intraocular lens 300 to be achieved with a smaller amount of ocular force.

Optic 402 may be molded directly onto haptic 404. Alternatively, optic 402 may be formed or fabricated separately from haptic 404, and then attached to haptic 404. In certain embodiments, haptic 404 is first machined or molded, and then optic 402 is molded and/or machined over or on top of haptic 404.

Optic 402 is preferably made from a relatively soft material, so that it can deform or change shape readily under the limited deforming forces produced by the capsular bag and/or ciliary muscle. An exemplary material is a relatively soft silicone material, although other suitable materials may be used as well. The stiffness of optic 402 may be less than 500 kPa, preferably from 0.5 kPa to 500 kPa. In some embodiments, the stiffness of optic 402 is between 25 kPa and 200 kPa or between 25 kPa and 50 kPa.

In contrast with optic 402, at least portions of haptic 404 (e.g., arms 412) are generally made of a relatively stiffer material than optic 402 material, so that haptic 404 can efficiently transmit ocular forces to optic 402. A relatively stiff silicone material can be used, although other suitable materials may be used as well, such as acrylic, polystyrene, or clear polyurethanes. The stiffness of haptic 404 may be greater than or equal to 500 kPa, or greater than or equal to 3000 kPa.

Arms 412 protrude or extend into optic 402 that include the clear aperture of optic 402. As used herein, the term "clear aperture" means the area of a lens or optic that restricts the extent of a bundle of rays from a collimated source or a distant light source that can imaged or focused by the lens or optic. The clear aperture is usually circular and is specified by its diameter. In some embodiments, the clear aperture has the same or substantially the same diameter as the optic. Alternatively, the diameter of the clear aperture may be smaller than the diameter of the optic, for example, due to the presence of a glare or PCO reducing structure disposed about a peripheral region of the optic.

Since inner structure 408 and the proximal ends 414 of arms 412 are located inside optic 402 and within the clear aperture thereof, at least these portions of haptic 404 are beneficially transparent or nearly transparent, so that it does not substantially block or scatter any light transmitted through optic 402. In addition, these portions of haptic 404 may have a refractive index that matches the refractive of optic 402 material so that interfaces between optic 402 and haptic 404 do not produce significant reflections or refractions that might produce scattered light within the eye, which might appear as a glare or haze to the patient.

A numerical example may be used to illustrate the effect of mismatch of refractive indices on reflected power. For a planar interface at normal incidence between air (refractive index of 1) and glass (refractive index of 1.5), 4% of the incident power is reflected at the interface. For such an interface between air and glass, there is no attempt to match refractive indices, and this 4% reflection will merely provide a baseline for comparison. If, instead of 1 and 1.5, the refractive indices differ by 4%, such as 1.5 and 1.56 or 1.5 and 1.44, there is a 0.04% reflection, or a factor of 100 improvement over air/glass. Finally, if the refractive indices differ by only 0.3%, such as 1.5 and 1.202 or 1.5 and 1.495, there is a 0.00028% reflection, or a factor of over 14000 improvement over air/glass. In practice, tolerances such as the 0.3% case may be achievable, and it is seen that a negligible fraction of power may be reflected at the interface between a haptic and an optic whose refractive indices differ by 0.3%. Note that the above base value of 1.5 was chosen for simplicity, and that haptic 404 and optic 402 may have any suitable refractive index.

Thus, the refractive indices of optic 402 and at least portions of haptic 404 inside optic 402 are equal or essentially the same. For the purposes of this document, "essentially the same" means that their refractive indices are equal to each other at a wavelength within the visible spectrum (i.e., between 400 nm and 700 nm). Note that haptic 404 and optic 402 may optionally have different dispersions, where the refractive index variation, as a function of wavelength, may be different for the haptic and the optic. In other words, if the refractive indices of haptic 404 and optic 402 are plotted as a function of wavelength, they may or may not have different slopes, and if the two curves cross at one or more wavelengths between 400 nm and 700 nm, then the refractive indices may be considered to be essentially the same or essentially equal.

The extension of arms 412 into optic 402 generally allows more effective transfer of radial forces along arms 412 to optic 402, since the inner diameter of inner structure 408 is less than the overall or outer diameter of optic 402. The relatively small "active area" of optic 402 located inside inner structure 408 allows ocular forces to be distributed over a smaller peripheral zone about the active area than if the same force were distributed over a periphery of the outer diameter, or a larger diameter, of optic 402. Since ocular forces are effectively concentrated over a relatively small area in the illustrated embodiment, this increases the pressure near the center of optic 402, which in turn increase the amount of curvature change or optical power change induced for a given amount of radial force on outer structure 410 and arms 412. As a result, the limited ciliary muscle or capsular bag force may produce a greater accommodative power change and/or axial translation optic 402. As used herein the term "active area" of an optic means a pupil of an optic over which a clinically significant change in optical power occurs in reaction to an ocular force generally sufficient to produce near vision in a human eye (e.g., an ocular force of 10 grams force).

The inner diameter of inner structure 408 is generally selected to be at least large enough that the active area of optic 402 can provide a change in optical power under scotopic lighting conditions (e.g., with a pupil diameter of the eye of 2 millimeters to 3 millimeters). For example, when intraocular lens 400 is used in a human eye, the active area is generally sufficiently large when the inner diameter of inner structure 408 is between 2 millimeters and 4 millimeters, or between 2.5 millimeters and 3.5 millimeters, or 3 millimeters plus or minus 0.25 millimeters.

In some embodiments, the axial thickness of inner structure 408 portion between arms 412, and/or overlapping proximal ends 414, is relatively large, for example, to help distribute more radial force on outer structure 410 into forces that change the shape of the anterior and posterior surfaces of optic 402. In some embodiments, the ratio of the optic center thickness to the axial thickness of inner structure 408 is less than or equal to 2. In other embodiments, greater accommodative power change in optic 402 is provided when the ratio of the optic center thickness to the axial thickness of inner structure 408 is less than 1.8 or less than 1.5.

As illustrated in FIGS. 4A-4C, the inner structure 408 may be in the form of a continuous ring and may generally have a radial thickness that is from 0.1 millimeters to 0.2 millimeters or of about 0.15 millimeters (e.g., 0.15 millimeters plus or minus 0.03 millimeters). The continuous ring form of inner structure 408 can provide structural stability to the optic when deformed during accommodation. Alternately, the inner structure 408 may be discontinuous as further discussed below in connection with FIGS. 6A-6F. The inner structure 408 can have a relatively small radial thickness to reduce the stiffness of inner structure 408, so that more of the radial forces transferred from arms 412 can be used to change the shape and accommodative optical power of optic 402. In some embodiments, outer structure 410 can be broken at predetermined locations or have a reduced axial thickness relative to the axial thickness of the remaining portions of outer structure 410.

As seen in FIG. 4B, arms 412 may be bifurcated or split at their distal ends 416 to form openings 418. Openings 418 may have a triangular shape, as shown in the illustrated embodiment. Alternatively openings 418 may have a different shape, for example, an oval shape (for example, as illustrated in FIGS. 3A and 3B). Opening 418 may be configured to reduce the mass of haptic 404, help direct radial forces toward inner structure 408, and/or control the shape of outer structure 410 during accommodation (e.g., help avoid bending or buckling). In some embodiments, some or all openings 418 are replaced regions of reduced axial thickness relative to a characteristic axial thickness of the remaining portions of arms 412. In other embodiments, outer structure 410 is either broken in the regions of openings 418 or has a reduced axial thickness relative to the axial thickness of the remaining portions of outer structure 410.

Outer structure 410 of haptic 404 mechanically couples intraocular lens 400 to capsular bag 18. Outer structure 410 may be in the form of a continuous ring and may generally have an axial thickness that is large enough to engage the equatorial region of capsular bag 18 over an area that is large enough to prevent tearing of the bag and to effectively couple ocular forces produced by capsular bag 18 to optic 402. In this regard, outer structure 410 may have an axial thickness that is from 0.5 millimeters to 1.0 millimeters or about 0.75 millimeters (e.g., 0.75 millimeters plus or minus 0.10 millimeters). In some embodiments, outer structure 410 has a radial thickness that is from 0.1 millimeters to 0.2 millimeters or about 0.15 millimeters (e.g., 0.15 millimeters plus or minus 0.03 millimeters). While the continuous ring form of outer structure 410 favorably helps to prevent buckling of AIOL 400, it has been discovered that a relatively small radial thickness reduces the stiffness of outer structure 410 so that radial forces are more effectively transferred along arms 412 and into the active area of optic 402. The outer structure 410 may be circular, elliptical, oval or polygonal (as shown in FIGS. 4A and 4B) in shape.

Referring to FIG. 4C, at least one of the edges of outer structure may have a discontinuity or sharp edge corner 422, for example, to help prevent PCO. Generally, sharp edge corner 422 has a radius that is less than 500 nanometers, preferably less than 400 nanometers. Additionally or alternatively, the side wall of optic 402 intersects the anterior face or posterior face of optic 402 to form a discontinuity or sharp edge corner that generally has a radius of curvature that is less than 500 nanometers, preferably less than 400 nanometers.

Outer structure 410 may be configured to have two outer diameters D1, D2, where D2 is greater than D1. In the illustrated embodiment, D1 is the outer diameter of outer structure 410 along opposite pairs of arms 412, while D2 is the outer diameter of outer structure 410 between adjacent pairs of arms 412. D1, D2 are advantageously selected to allow the AIOL 400 to accommodate a range of capsular bag sizes that is generally superior to a substantially equivalent outer structure that is circular or even oval in shape, or that includes indents that protrude inwardly toward the center of the intraocular lens. For example, the larger diameter D2 provides for at least portions of a capsular bag having a diameter of, or about equal to, D2 to contact the outer structure 410 when the eye is in a disaccommodative state, whereby accommodative forces may be effectively transmitted to optic 402. Alternatively, if the capsular bag has a diameter of, or about equal to, D1, then the capsular bag will contact the outer structure about its entire circumference. The capsular bag may be slightly taut over portions of ring 402 having the diameter D2, but the overall stress on the capsular bag is less than that experienced for a ring having a constant outer diameter of D2. Accordingly, the outer structure 410 of AIOL 400 is favorably configured to accommodate a larger variation of bag sizes than a substantially equivalent intraocular lens having an outer structure with a constant outer diameter. In certain embodiments, the outer diameter D2 is between 20 microns and 500 microns greater than the outer diameter D1, preferably between 40 microns and 250 microns greater than the outer diameter D1.

In certain embodiments, optic 402 is a multifocal optic, changes from a monofocal optic to a multifocal optic, depending upon the amount of ocular force on haptic 404 and/or the state of accommodation of the eye into which AIOL 400 is inserted.

Figure 5A:
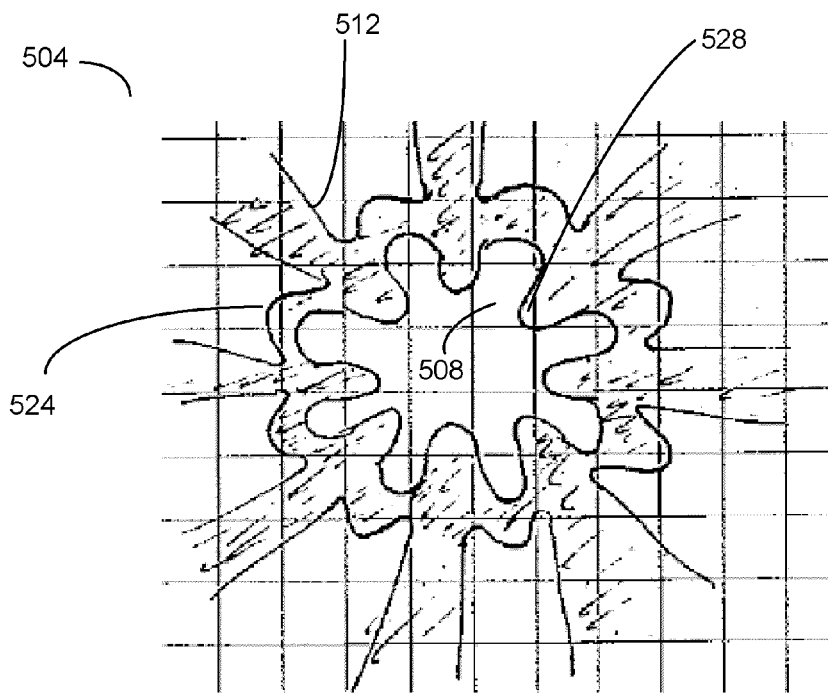
FIGS. 5A-5B illustrate various embodiments of haptics for accommodating intraocular lenses, the haptic including an inner ring that is sinusoidal in the radial direction.
Figure 5B:
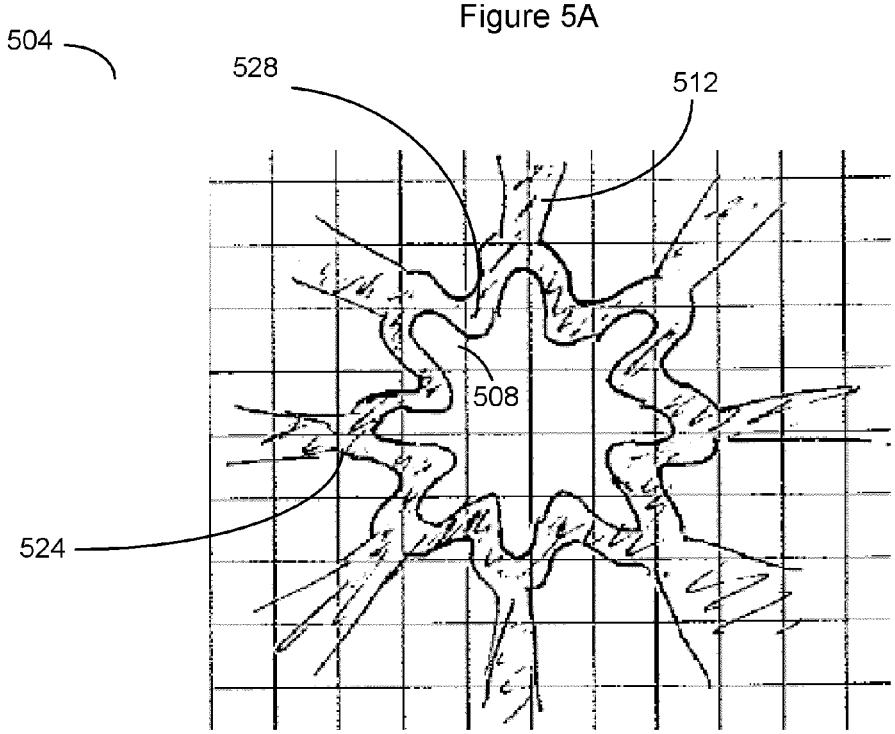

Instead of or in addition to an inner structure 408 that is sinusoidal in the axial direction as shown in FIGS. 4A-4C, the inner structure can be sinusoidal in the radial direction as illustrated in FIGS. 5A and 5B to enhance the ocular force transferred by the haptic to the optic and/or to achieve the same accommodative effect as any of the above disclosed embodiments with a smaller amount of compressive force.

The embodiments illustrated in FIGS. 5A and 5B include a haptic 504 that can be coupled to an optic (for example, optic 402 described above). The haptic 504 includes a plurality of arms 512. Each of the arms 512 is connected to an inner structure 508 that is configured to be disposed adjacent to an optic (for example, optic 402 described above). In various embodiments, a portion of the plurality of arms 512 and/or the inner structure 508 can protrude into the optic. Where appropriate, structures and features of the haptic 304, 404 discussed above may be incorporated in the haptic 504. For example, the haptic 504 may be made of the same or similar materials as those discussed for haptic 304 and 404. Except where indicated otherwise, dimensions of haptic 304 and 404 may be incorporated into haptic 504 (e.g., the thickness or other dimensions of inner structure 508 may be the same or similar to those illustrated and discussed for inner structure 308 and 408; the shape and/or size of at least portions of arms 512 may be the same or similar to those illustrated and discussed for arms 312 and 412; and the like) and vice-versa.

As illustrated in FIGS. 5A and 5B, the inner structure 508 of the haptic 504 can be a sinusoidal ring having a plurality of peaks/crests 524 and a plurality of valleys/troughs 528 disposed about a center of the sinusoidal ring. In various embodiments, the plurality of peaks/crests 524 can be disposed at a fixed radial distance R1 from the center of the sinusoidal ring while the plurality of valleys/troughs 528 can be disposed at a fixed radial distance R2 from the center of the sinusoidal ring such that R2<R1. Accordingly, the plurality of peaks/crests 524 and the plurality of valleys/troughs 528 are arranged symmetrically around the center of the sinusoidal ring such that the sinusoidal ring can symmetrically deform an optic when the optic is disposed such that the center of the optic coincides with the center of the sinusoidal ring. However, in other embodiments, the plurality of peaks/crests 524 and the plurality of valleys/troughs 528 are arranged asymmetrically around the center of the sinusoidal ring such that the sinusoidal ring can asymmetrically deform an optic when the optic is disposed such that the center of the optic coincides with the center of the sinusoidal ring. In another embodiment, the inner structure 508 can be a wavy structure such that when coupled to an optic each of the peaks/crests 524 and each of the valleys/troughs 528 can be disposed at a varying distance from the optical axis of the optic.

In various embodiments, each of the plurality of haptic arms 512 can be connected to a valley/trough 528 of the sinusoidal ring as illustrated in FIG. 5A. This configuration will concentrate axial displacement of the optic surface into a small area, thus increasing the accommodation potential of the lens. Alternately, in various embodiments, each of the plurality of haptic arms 512 can be connected to a peak/crest 524 of the sinusoidal ring as illustrated in FIG. 5B. In this configuration, axial displacement of the optic surface will be distributed more evenly across the optic zone, thus minimizing optical distortion and artifacts caused by driving the optic to a compressed or accommodated state. In various embodiments of the haptic 504, the distal ends (farthest from the inner structure 508) of each of the plurality of haptic arms 512 may be connected to an outer structure that is similar to the outer structures 310, 410 described above. In various embodiments, each of the plurality of arms 512 may be connected together at an intermediate position between the distal end and a proximal end that is closest to the inner structure 508 by a supporting ring. In various embodiments, the inner structure 508 can be sinusoidal in the radial direction as illustrated in FIGS. 5A and 5B as well as in the axial direction as illustrated in FIGS. 4A-4C. Although, the inner structures 408 and 508 illustrated in FIGS. 4A-5B are shown as continuous, in various embodiments, the inner structures 408 and 508 may be discontinuous as discussed below to enhance compressibility and the ability to transfer ocular force to the optic.

B. Haptics Including a Discontinuous Structure Adjacent to the Optic

FIGS. 6A-6F illustrate various embodiments of an intraocular lens 600 comprising an optic 602 coupled to a haptic 604 configured to effectively transfer an ocular force from a human or animal eye to optic 602 so as to produce a range of powers in response to an ocular force. The haptic 604 includes a plurality of arms 612. Each of the plurality of arms 612 has a proximal end 614 that is adjacent to the optic 602 and an elongate body that extends away from the proximal end 614 along a radial direction towards a distal end 616. The distal end 616 of the haptic arms 612 can be joined together by an outer structure that is similar to the outer structures 310, 410 discussed above in connection with the embodiments illustrated in FIGS. 3A-4C. The plurality of haptic arms 612 can be bifurcated at the distal ends 616 as discussed above in connection with the embodiments illustrated in FIGS. 3A-4C. In various embodiments, each of the plurality of haptic arms 612 can be thicker at the distal end 616 as compared to the proximal end 614. In various embodiments, each of the plurality of haptic arms 612 can be thicker at the proximal end 614 as compared to the distal end 616. The distal ends 614 can have bulge out axially to engage the capsular bag 18 over a large surface area as discussed about in connection with FIGS. 3A and 3B and as disclosed in U.S. application Ser. No. 12/849,451 titled "Intraocular Lens and Methods for Providing Accommodative Vision," which published as U.S. Publication No. 2011/0040379. The entire disclosure of the above-mentioned application is incorporated herein by reference. The haptic 604 comprises a plurality of inner structures 608 that are adjacent the optic 602. Each of the plurality of inner structures 608 is connected to one of the plurality of haptic arms 612.

Accommodating IOL 600 is similar to the accommodating IOL 300 or 400 in many ways; however, also includes design features that are configured to alter the way in which forces are transferred from haptic 604 to optic 602, or to otherwise alter performance and/or function. Where appropriate, structures and features of accommodating IOL 300 or 400 are discussed above may be incorporated into accommodating IOL 600. For example, accommodating IOL 600 may be made of the same or similar materials as those discussed for accommodating IOL 300 or 400. Except where indicated otherwise, dimensions of accommodating IOL 300 or 400 may be incorporated into embodiments according to accommodating IOL 600 (e.g., the thickness or other dimensions of inner structure 608 may be the same or similar to those illustrated and discussed for inner structure 308, 408 and/or 508; the shape and/or size of at least portions of arms 612 may be the same or similar to those illustrated and discussed for arms 312, 412 and/or 512; and the like) and vice-versa.

As discussed above, the haptic arms 612 and the inner structure 608 can be stiffer than the optic 602 to effectively and efficiently transfer the ocular to the optic 602 and provide accommodation. In various embodiments, as discussed above, the refractive index of at least the proximal end 614 of the haptic arms 612 and the inner structure 608 can be approximately equal to the refractive index of the optic 602 to reduce or eliminate glare or haze when the accommodating IOL 600 is implanted in a patient's eye.

Figure 6A:
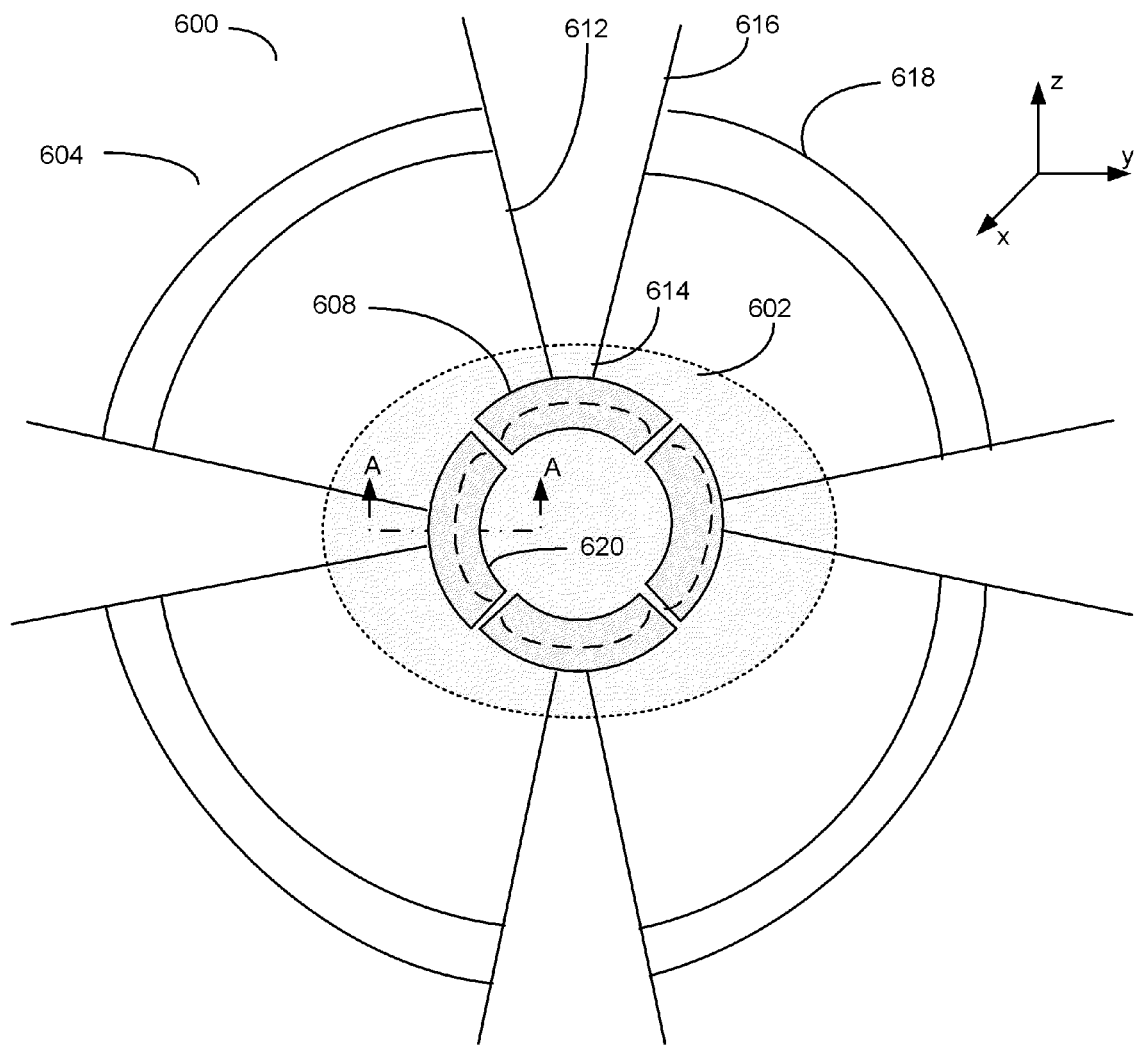
FIGS. 6A-6F illustrate various embodiments of an accommodating intraocular lens comprising a haptic coupled to an optic, the haptic including a discontinuous inner structure.
Figure 6B:
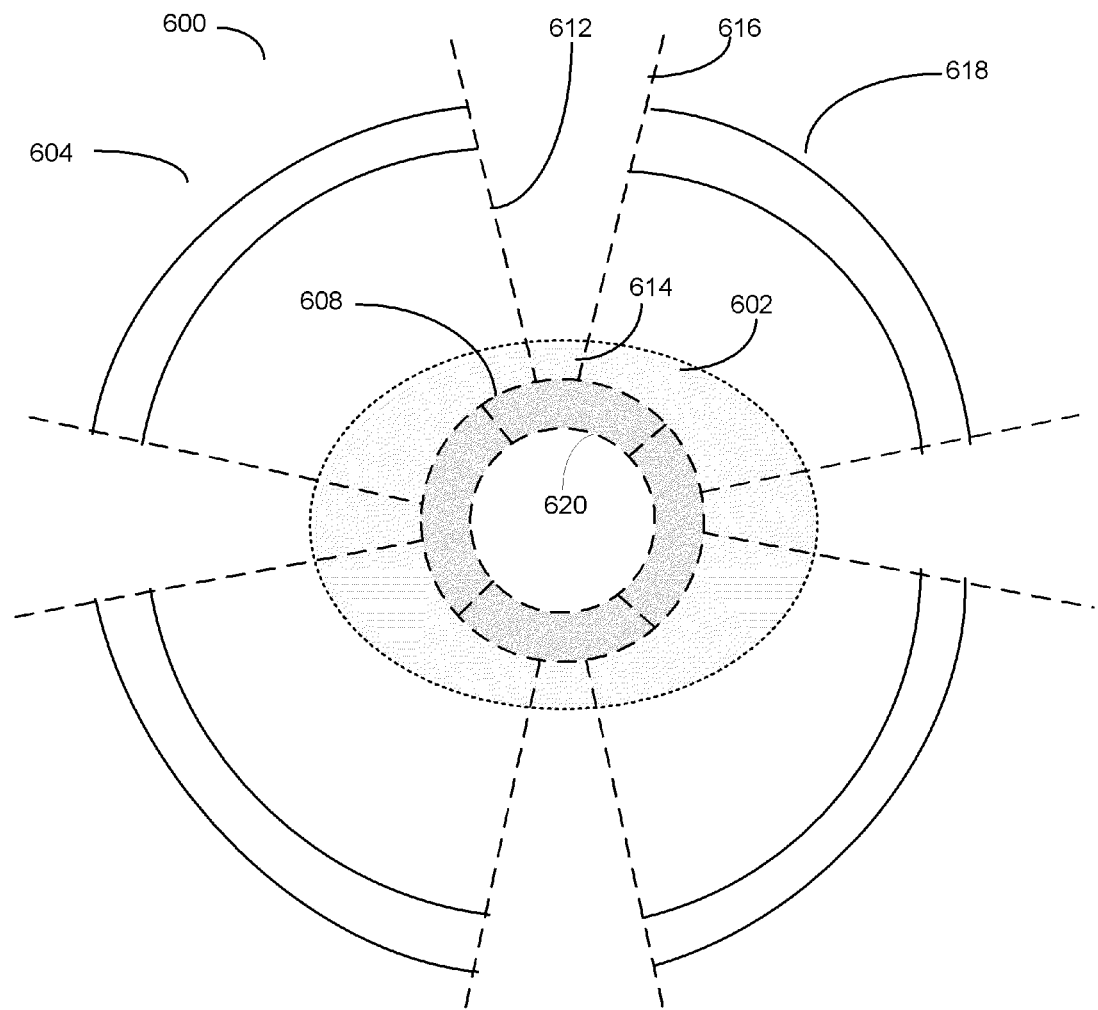
Figure 6C:
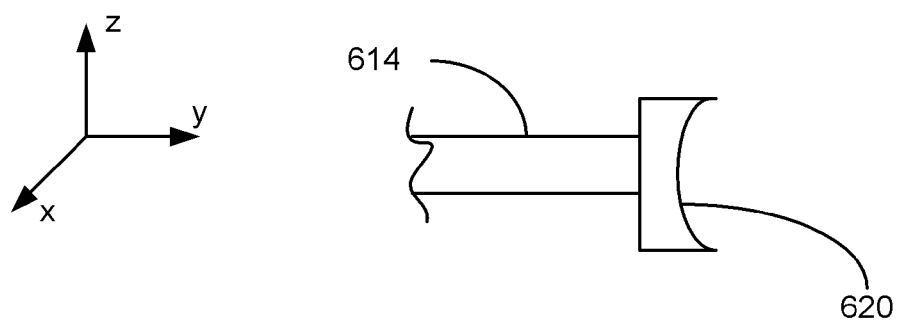
Figure 6D:
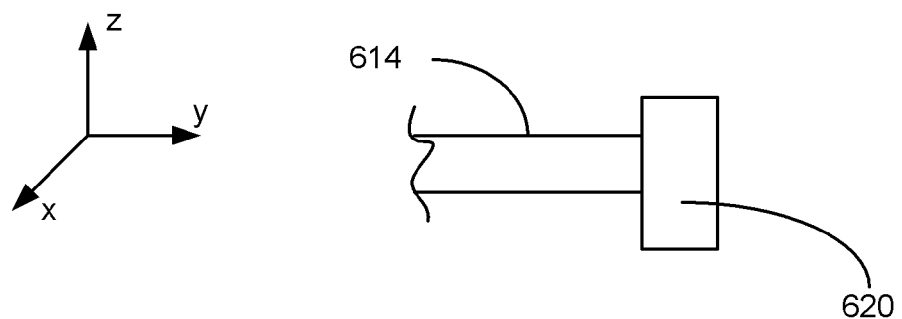

In various embodiments, the proximal end of the haptic arms 612 and the plurality of inner structures 608 can protrude into the optic 602 as illustrated in FIG. 6A. In other embodiments, the plurality of the inner structures 608 can be disposed such that they are in contact with an outer edge or periphery of the optic 602. In various embodiments, a portion 620 that is adjacent the optic 602 of at least some of the plurality of inner structures 608 can be curved in the radial and/or the axial direction as illustrated in FIGS. 6B-6C. The curved surface 620 can have a parabolic, elliptical or hemispherical shape. FIG. 6C illustrates a cross-sectional view of the portion 620 in the z-y plane through the axis A-A. As seen from the cross-sectional view, the portion 620 is curved in the radial direction.

The plurality of inner structures 608 is disposed such that each of the plurality of inner structures 608 is separated or disjoint from an adjacent inner structure in the unaccommodated state. Under the influence of ocular forces, the plurality of inner structures 608 can move or deform (for example, stretch or extend) such that the plurality of inner structures 608 meet or are joined together to form a ring having a continuous periphery in the fully compressed or accommodated state. The compressive forces exerted on the plurality of inner structures 608 can be efficiently transferred to the relatively soft optic 602 and cause it to deform (or "bulge out") during accommodation.

Figure 6E:
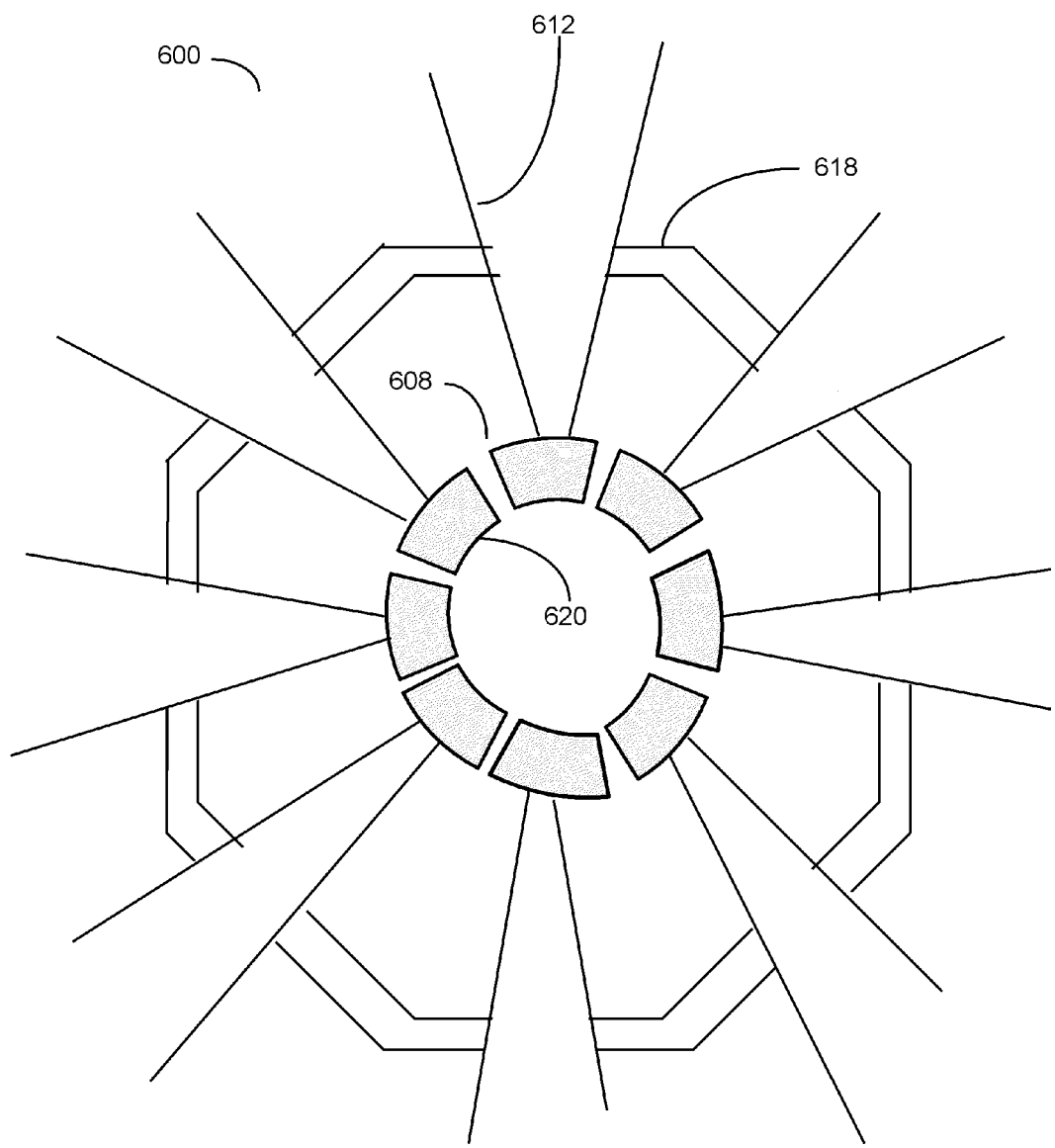
Figure 6F:
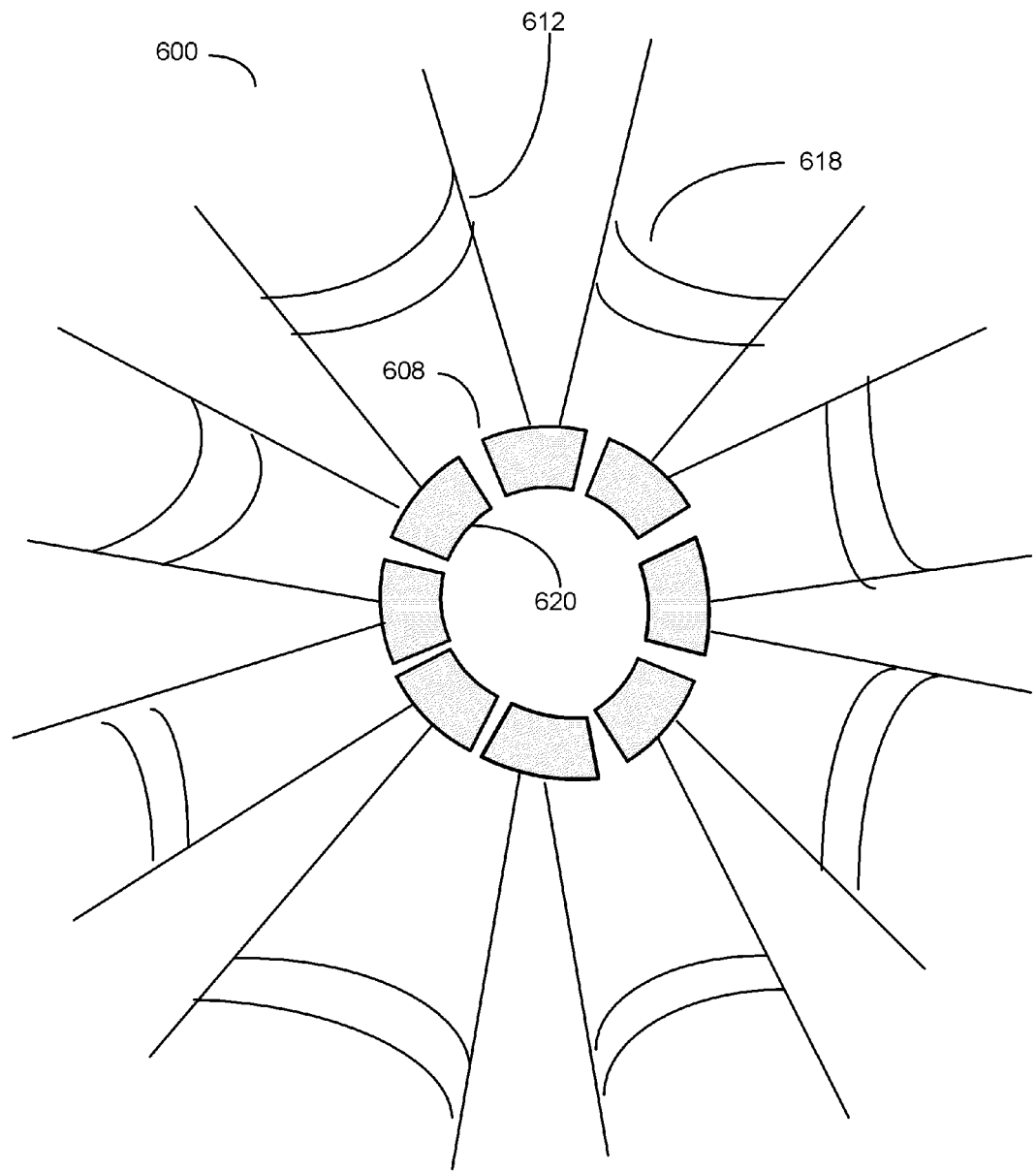

In various embodiments, the haptic 604 can include four haptic arms 612 coupled to four inner structures 608 as shown in FIG. 6A. In other embodiments, the haptic 604 can include eight haptic arms 612 coupled to eight inner structures 608 as shown in FIGS. 6E and 6F. In various other embodiments, the number of haptic arms 612 and the inner structures 608 can be 2, 6, 10, 12, etc. The number of haptic arms 612 and the inner structures 608 can depend on various factors such as the haptic design, haptic material, condition of the patient's eye, desired accommodation range, etc. In various embodiments, increasing the number of arms can make displacement of the optic more uniform (yielding a more uniform image with fewer aberrations) and would make lens performance less sensitive to asymmetric ocular forces which might occur when one or more zonules are broken or when the capsular bag is damaged in some way In various embodiments, the plurality of the haptic arms 612 may be joined together or connected by segments 618 that are disposed between the proximal end 614 and the distal end 616. In various embodiments, the segments 618 can provide stability to the plurality of haptic arms 612. The segments 618 can be thinner than the haptic arms 612 and be relatively more flexible than the haptic arms 612 so that the segments 618 do not adversely affect the ability of the haptic arms 612 to provide accommodation. In various embodiments, the segments 618 can be arcuate and curve towards the optic 602, as illustrated in FIG. 6A. In some embodiments the arcuate segments 618 can curve away from the optic 602, as illustrated in FIG. 6F. In some embodiments, the segments 618 can be linear and form an octagonal supporting structure as shown in FIG. 6E (if the number of arms 612 is eight, as illustrated in FIG. 6E). In various embodiments, the segments 618 can form a hexagonal supporting structure (if the number of arms 612 is six), a decagonal supporting structure (if the number of arms 612 is ten), an elliptical supporting structure, etc.

The description of the embodiments and their applications as set forth herein is illustrative and is not intended to limit the scope of the claims. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:
1. An intraocular lens, comprising:
    an optic adapted to focus light on the retina when disposed in the eye, the optic having an adjustable zone intersected by a central optical axis of the optic; and
    a haptic, comprising:

an inner annular member disposed adjacent to or inside the adjustable zone of the optic, the inner annular member comprising a continuous inner perimeter in the shape of a ring in a fully compressed state and a discontinuous inner perimeter in a relaxed state comprised of a plurality of spaced apart arcuate segments; and a plurality of arms extending away from the inner annular member;

wherein the intraocular lens is adapted to respond to ocular forces to adjust the power of the optic from a distance vision power in the relaxed state to a near vision power in a fully accommodated state.

2. The intraocular lens of claim 1, wherein each of the arms comprises a proximal end extending away from an outer side of the inner annular member.

3. The intraocular lens of claim 2, wherein a distal end of each of the arms is coupled with a continuous ring.

4. The intraocular lens of claim 3, wherein the continuous ring comprises a plurality of straight segments extending transverse to a longitudinal axis of each arm, the straight segments being joined at a location between adjacent arms.

5. The intraocular lens of claim 3, wherein the continuous ring comprises a wavy member comprising at least one inflection disposed between adjacent arms.

6. The intraocular lens of claim 5, wherein the continuous ring comprises a sinusoidal configuration.

7. The intraocular lens of claim 1, wherein each arm of the plurality of arms extends along a direction perpendicular to the optical axis.

8. The intraocular lens of claim 1, comprising eight arms spaced apart by a constant amount extending symmetrically away from the adjustable zone.

9. The intraocular lens of claim 1, wherein the adjustable zone is adapted to provide at least 2 Diopters of add power.

10. An intraocular lens, comprising:
an optic disposed about a central optical axis and adapted to focus light on the retina when disposed in the eye, the optic having an adjustable zone; and
a haptic, comprising:
a plurality of arms, each arm having an inner end coupled to an inner member with an elongate body extending away from the inner end, wherein the inner member comprises a continuous inner surface surrounding the adjustable zone, the inner surface being located a varying distance from the central optical axis and configured in a sinusoidal configuration when viewed from a top plan view;
wherein the intraocular lens is adapted to respond to ocular forces to adjust the power of the optic from a distance vision power zone toward a near vision power.

11. The intraocular lens of claim 10, wherein each of the arms is coupled with a peak of the sinusoidal inner member.

12. The intraocular lens of claim 10, wherein each of the arms is coupled with a valley of the sinusoidal inner member.

13. The intraocular lens of claim 10, wherein each of the arms extends away from an outer portion of the inner member corresponding to a portion of the inner surface that is spaced farther away from the central optical axis than are adjacent portions of the inner surface.

14. The intraocular lens of claim 10, wherein each of the arms extends away from an outer portion of the inner member corresponding to a portion of the inner surface that is closer to the central optical axis than are adjacent portions of the inner surface.

15. An intraocular lens, comprising:
a deformable optic having a relaxed configuration including a first radius of curvature characteristic and a compressed configuration including a second radius of curvature characteristic, the deformable optic adapted to be deformed from the relaxed configuration to the compressed configuration by ocular forces; and
a plurality of haptic arms that can engage and apply a radial compressive force to axially deform the deformable optic, each of the plurality of haptic arms including a proximal arcuate section that can engage an outer or an inner periphery of the deformable optic and a distal portion that can engage an evacuated capsular bag, the proximal arcuate section of each of the plurality of haptic arms including an arcuate region, wherein the proximal arcuate sections of each of the plurality of haptic arms are spaced apart when in the relaxed configuration and wherein the proximal arcuate sections of each of the plurality of haptic arms can join to form a continuous structure in the shape of a ring when the deformable optic is in the compressed configuration.

16. The intraocular lens of claim 15, further including an outer ring connecting the distal portions of each of the plurality of haptic arms.

17. The intraocular lens of claim 16, wherein the outer ring includes a plurality of straight segments extending transverse to a longitudinal axis of each arm, the straight segments being joined at a location between adjacent arms.

18. The intraocular lens of claim 16, wherein the outer ring comprises a wavy member comprising at least one inflection disposed between adjacent haptic arms.

19. The intraocular lens of claim 16, wherein the outer ring comprises a sinusoidal configuration.

* * * * *